US012004890B2

(12) United States Patent
Capo et al.

(10) Patent No.: US 12,004,890 B2
(45) Date of Patent: Jun. 11, 2024

(54) INTRAORAL TOMOSYNTHESIS X-RAY IMAGING DEVICE, SYSTEM, AND METHOD WITH INTERCHANGEABLE COLLIMATOR

(71) Applicant: XIN VIVO, INC., Morrisville, NC (US)

(72) Inventors: Captain Capo, Durham, NC (US); Andrew Tucker, Cary, NC (US); Julianna Burney, Cary, NC (US); Otto Z. Zhou, Chapel Hill, NC (US); Jianping Lu, Chapel Hill, NC (US)

(73) Assignee: Surround Medical Systems, Inc., Morrisville, NC (US)

( * ) Notice: Subject to any disclaimer, the term of this patent is extended or adjusted under 35 U.S.C. 154(b) by 495 days.

(21) Appl. No.: 17/288,556

(22) PCT Filed: Oct. 26, 2018

(86) PCT No.: PCT/US2018/057719
§ 371 (c)(1),
(2) Date: Apr. 25, 2021

(87) PCT Pub. No.: WO2020/086094
PCT Pub. Date: Apr. 30, 2020

(65) Prior Publication Data
US 2022/0110595 A1   Apr. 14, 2022

(51) Int. Cl.
*A61B 6/51* (2024.01)
*A61B 6/00* (2006.01)
(Continued)

(52) U.S. Cl.
CPC .............. *A61B 6/512* (2024.01); *A61B 6/022* (2013.01); *A61B 6/025* (2013.01); *A61B 6/06* (2013.01);
(Continued)

(58) Field of Classification Search
CPC ......... A61B 6/145; A61B 6/022; A61B 6/025; A61B 6/06; A61B 6/4007; A61B 6/425; A61B 6/461; A61B 6/469; A61B 6/56
See application file for complete search history.

(56) References Cited

U.S. PATENT DOCUMENTS 5,549,439 A   8/1996   Ploem
5,762,608 A   6/1998   Warne et al.
(Continued)

FOREIGN PATENT DOCUMENTS

CA   3009090 A1   8/2017
CA   3011305 A1   8/2017
(Continued)

OTHER PUBLICATIONS

International Search Report and Written Opinion for Application No. PCT/US2017/016011 dated Jul. 28, 2017.
IPRP for PCT/US2018/057719.

*Primary Examiner* — David P Porta
*Assistant Examiner* — Fani Polyzos Boosalis
(74) *Attorney, Agent, or Firm* — Talus Law Group LLC (57) ABSTRACT

An intraoral tomosynthesis x-ray imaging device, system, and method with an interchangeable collimator. The intraoral tomosynthesis x-ray imaging device includes an x-ray source array including one or more spatially distributed focal spots and a detachable collimation assembly to provide rectangular or circular radiation fields. The intraoral tomosynthesis x-ray imaging device further includes a digital intraoral x-ray detector. In some embodiments, the x-ray source array is configured to produce either a scanning x-ray beam illuminating an object from different viewing angles without mechanically moving the x-ray source array for tomosynthesis, or a single two-dimensional radiograph.

24 Claims, 10 Drawing Sheets

(51) Int. Cl.
*A61B 6/02* (2006.01)
*A61B 6/06* (2006.01)
*A61B 6/40* (2024.01)
*A61B 6/42* (2024.01)
*A61B 6/46* (2024.01)

(52) U.S. Cl.
CPC ............ *A61B 6/4007* (2013.01); *A61B 6/425* (2013.01); *A61B 6/461* (2013.01); *A61B 6/469* (2013.01); *A61B 6/56* (2013.01)

(56) References Cited

U.S. PATENT DOCUMENTS

| | | |
|---|---|---|
| 6,760,407 B2 | 7/2004 | Price |
| 7,187,756 B2 | 3/2007 | Gohno et al. |
| 7,697,658 B2 | 4/2010 | Wang et al. |
| 7,751,528 B2 | 7/2010 | Zhou |
| 7,771,117 B2 | 8/2010 | Kim et al. |
| 7,773,721 B2 | 8/2010 | Wu et al. |
| 7,809,114 B2 | 10/2010 | Zou et al. |
| 7,826,594 B2 | 11/2010 | Zou et al. |
| 8,094,773 B2 | 1/2012 | Boese et al. |
| 8,428,219 B2 | 4/2013 | Friedrich |
| 8,491,188 B2 | 7/2013 | Vogtmeier et al. |
| 8,559,591 B2 | 10/2013 | Boese et al. |
| 8,576,988 B2 | 11/2013 | Lewalter et al. |
| 8,670,521 B2 | 3/2014 | Bothorel et al. |
| 8,787,523 B2 | 7/2014 | Sackett |
| 8,817,947 B2 | 8/2014 | Vedantham et al. |
| 8,855,393 B2 | 10/2014 | Bultema |
| 9,217,719 B2 | 12/2015 | Lowell et al. |
| 9,401,019 B2 | 7/2016 | Dennerlein et al. |
| 9,733,198 B2 | 8/2017 | Lowell et al. |
| 10,165,993 B2 | 1/2019 | Kim et al. |
| 10,327,718 B2 | 6/2019 | Kim et al. |
| 10,456,097 B2 | 10/2019 | Kim et al. |
| 10,492,736 B2 | 12/2019 | Papalazarou et al. |
| 10,980,494 B2 * | 4/2021 | Lu .................... A61B 6/482 |
| 2007/0009088 A1 | 1/2007 | Edic et al. |
| 2007/0273945 A1 | 11/2007 | Furman |
| 2008/0023636 A1 | 1/2008 | Chowdhury et al. |
| 2010/0034450 A1 | 2/2010 | Mertelmeier |
| 2010/0040203 A1 | 2/2010 | Ayraud |
| 2011/0150185 A1 | 6/2011 | Uzbelger |
| 2012/0087464 A1 | 4/2012 | McCroskey et al. |
| 2012/0305812 A1 | 12/2012 | Bowen et al. |
| 2014/0050298 A1 | 2/2014 | Lee |
| 2015/0320371 A1 | 11/2015 | Heath et al. |
| 2015/0359504 A1 | 12/2015 | Zhou et al. |
| 2016/0262710 A1 | 9/2016 | Baek et al. |
| 2016/0310088 A1 | 10/2016 | Kim et al. |
| 2016/0317107 A1 | 11/2016 | Zhou et al. |
| 2016/0338657 A1 | 11/2016 | Kim et al. |
| 2017/0164910 A1 | 6/2017 | Cao et al. |
| 2017/0245813 A1 | 8/2017 | Choi |
| 2017/0319160 A1 | 11/2017 | Lu et al. |
| 2018/0038807 A1 | 2/2018 | Hauser et al. |
| 2019/0001146 A1 | 1/2019 | Liu |
| 2019/0029611 A1 | 1/2019 | Travish et al. |
| 2019/0126070 A1 | 5/2019 | Hsieh |
| 2019/0209107 A1 | 7/2019 | Vogtmeier et al. |
| 2019/0252148 A1 | 8/2019 | Travish et al. |
| 2019/0265174 A1 | 8/2019 | Hauser et al. |
| 2019/0388050 A1 | 12/2019 | Lee et al. |
| 2020/0000423 A1 | 1/2020 | Mohammadi |
| 2020/0100746 A1 | 4/2020 | Sato et al. |
| 2020/0100749 A1 | 4/2020 | Makino et al. |
| 2020/0100753 A1 | 4/2020 | Radicke |
| 2020/0107794 A1 | 4/2020 | Mandelkern et al. |

FOREIGN PATENT DOCUMENTS

| | | |
|---|---|---|
| CA | 3030623 A1 | 2/2018 |
| CA | 3039309 A1 | 4/2018 |
| EP | 2102638 A1 | 9/2009 |
| EP | 2478547 A1 | 7/2012 |
| EP | 2948061 A2 | 12/2015 |
| EP | 2943781 A4 | 9/2016 |
| EP | 2244634 B1 | 11/2016 |
| EP | 3187112 A1 | 7/2017 |
| EP | 3066983 A4 | 8/2017 |
| EP | 2713886 B1 | 9/2017 |
| EP | 3103394 A4 | 12/2017 |
| EP | 3175792 A4 | 7/2018 |
| EP | 3210538 A4 | 9/2018 |
| EP | 3087923 B1 | 12/2018 |
| EP | 3407792 A1 | 12/2018 |
| EP | 3476298 A2 | 5/2019 |
| EP | 3496615 A1 | 6/2019 |
| EP | 3225164 B1 | 7/2019 |
| EP | 3529821 A1 | 8/2019 |
| EP | 3533396 A1 | 9/2019 |
| EP | 3062705 B1 | 10/2019 |
| EP | 3442426 A4 | 12/2019 |
| EP | 3576629 A1 | 12/2019 |
| EP | 3463090 B1 | 1/2020 |
| EP | 3586752 A1 | 1/2020 |
| EP | 3407793 B1 | 3/2020 |
| EP | 3618718 A1 | 3/2020 |
| EP | 3628229 A1 | 4/2020 |
| WO | WO 2015/111968 A1 | 7/2015 |
| WO | WO 2017/196413 A1 | 11/2017 |

* cited by examiner

INTRAORAL TOMOSYNTHESIS X-RAY IMAGING DEVICE, SYSTEM, AND METHOD WITH INTERCHANGEABLE COLLIMATOR

CROSS REFERENCE TO RELATED APPLICATIONS

This is a national stage application of PCT application No. PCT/2018/057719 having an international filing date of Oct. 26, 2018, the entire contents of which are incorporated herein by reference in its entirety for all purposes.

TECHNICAL FIELD

The subject matter disclosed herein relates generally to x-ray imaging. More particularly, the subject matter disclosed herein relates to stationary intraoral tomosynthesis systems, devices, and methods for three-dimensional dental imaging.

BACKGROUND OF THE INVENTION

Dental radiology has undergone important changes over the past several decades. However, the need for more precise diagnostic imaging methods continues to be a high priority. Intraoral dental X-rays were introduced only one year after Roentgen's discovery of X-ray radiation. Since that time, advances in dental imaging techniques have included more sensitive detector technology, panoramic imaging, digital imaging and Cone Beam Computed Tomography (CBCT). Computed Tomography (CT), Magnetic Resonance Imaging (MRI), Ultrasound (US), and optical techniques have also been investigated for dental imaging.

Intraoral radiography is the mainstay of dental imaging. It provides relatively high resolution, and limited field of view images for most routine dental needs. However, as a two dimensional (2D) imaging modality, the technique suffers from superimposition of overlying structures and loss of spatial information in the depth dimension. Panoramic imaging, a popular form of extraoral imaging, visualizes the entire maxilla, mandible, temporo-mandibular joints (TMJ), and associated structures in a single image. However, it is subject to considerable geometric distortion and has relatively low spatial resolution compared with intraoral radiography. CBCT as a three dimensional (3D) imaging modality has found wide acceptance in dentistry, especially for surgical planning procedures such as dental implant and orthodontic treatment planning, and evaluation of endodontic and pathological condition. There are, however, several disadvantages associated with CBCT in comparison to 2D radiography: (1) excess noise and artifacts from metal dental restorations/appliances reduce the image quality; (2) acquisition, reconstruction, and interpretation time are greatly increased, reducing clinical efficiency and increasing financial cost; and (3) significantly higher ionizing radiation doses increase the radiation burden for the patient.

Despite the many technological advances, the radiographic diagnostic accuracy for some of the most common dental conditions has not improved in many years and in some cases remains low. Examples include caries detection, root fracture detection, and assessment of periodontal bone loss.

Caries are the most common dental disease. The World Health Organizations estimates that 60-90% of school children and nearly all adults have dental caries at some point in time. If carious lesions are detected early enough, i.e. before cavitation, they can be arrested and re-mineralized by non-surgical means. When carious lesions go undetected, they can evolve into more serious conditions that may require large restorations, endodontic treatment, and, in some cases, extractions. The detection sensitivity of caries has not seen any significant improvement in the past several decades. 2D intraoral radiography is the current gold standard, with a reported sensitivity ranging from 40% to 70% for lesions into dentine and from 30% to 40% for lesions confined to enamel. CBCT does not provide significant improvement for caries detection. Beam-hardening artifacts and patient movement decrease structure sharpness and definition.

The detection of vertical root fractures (VRF) represents a clinically significant diagnostic task with important ramifications in tooth management. VRFs are considered one of the most frustrating tooth conditions associated with endodontic therapy. Overall detection of VRFs remains poor. The ability of CBCT to detect initial small root fractures is limited by its relatively low resolution.

Dental radiography provides important information for assessing tooth prognosis and making treatment decisions associated with periodontal disease. Currently, 2D intraoral radiography is the mainstay of dental imaging. It provides relatively high resolution images with a limited field of view for most routine dental needs. However, this technique is limited because of the 2D representation of 3D objects. The 2D image results in superimposition of overlying structures and loss of spatial information in the depth dimension. Consequently, important dimensional relationships are obscured, observed sharpness is reduced, objects of interest are lost, and pathology contrast is reduced. On the other hand, Panoramic imaging, a popular form of extra-oral imaging visualizes the entire maxilla, mandible, temporo-mandibular joints and associated structures on a single scan. It is subject to considerable geometric distortion, and has relatively low spatial resolution compared with intraoral radiography.

These diagnostic tasks illustrate the clinical need for a diagnostic imaging system with high resolution, 3D capabilities, reduced metal artifact and lower radiation burden to patients.

Digital tomosynthesis imaging is a 3D imaging technique that provides reconstruction slice images from a limited-angle series of projection images. Digital tomosynthesis improves the visibility of anatomical structures by reducing visual clutter from overlying normal anatomy. Some examples of current clinical tomosynthesis applications include chest, abdominal, musculoskeletal, and breast imaging.

A variation of the tomosynthesis technique, called Tuned Aperture Computed Tomography (TACT), was investigated in the late 1990's for dental imaging. TACT significantly improved the diagnostic accuracy for a number of tasks compared to conventional radiography. These included: (1) root fracture detection, (2) detection and quantification of periodontal bone loss, (3) implant site assessment, and (4) the evaluation of impacted third molars. The results for caries, however, were inconclusive.

TACT was not adopted clinically because the technology was not practical for patient imaging. Conventional x-ray tubes are single pixel devices where x-rays are emitted from a fixed point (focal spot). To acquire the multiple projection images, an x-ray source was mechanically moved around the patient. A fiducial marker was used to determine the imaging geometry. The process was time consuming (e.g., approximately 30 minutes per scan) and required high operator skill to accomplish image acquisition. The difficulty of determining precisely the imaging geometry parameters and long imaging acquisition time due to mechanical motion of the source makes TACT impractical. Any variation of TACT for 3D intraoral imaging using a single x-ray source suffers from similar drawbacks and disadvantages.

Extra-oral tomosynthesis has been investigated in a patient study using an experimental device as well as by using CBCT. The extra-oral geometry required high radiation doses. The image quality was compromised by crosstalk of out-of-focus structures. In order to avoid high radiation doses, intraoral tomosynthesis using a single mechanically scanning x-ray source has been described in the patent literature, and investigated in a recent publication using a single conventional x-ray source and a rotating phantom. Unfortunately, the limitations described above for TACT remained the same for these approaches, which are caused primarily by the conventional single focal spot x-ray tube.

The concept of a stationary intraoral tomosynthesis system has recently been disclosed in U.S. Pat. Nos. 9,782,136, and 9,907,520. The system utilizes a distributed x-ray source array to generate all the projection images needed for reconstruction without any mechanical movement of the source or the detector. The x-ray source array is placed outside a patient's mouth and an intraoral detector placed inside the patient's mouth. Such a distributed x-ray source array can now be constructed using, for example, carbon nanotube (CNT) field emission x-ray technology. The feasibility of this technology has been demonstrated and reported in several research publications and in clinical studies.

As all existing commercial intraoral imaging systems are 2D regular radiographic imaging devices, when adopting new imaging devices such as the intraoral tomosynthesis imaging system of the present disclosure, there is a desire from dentists and practitioners that the same system be capable of performing intraoral imaging in both the tomosynthesis mode and in the regular 2D radiographic mode.

A medical imaging device should follow the principle of As Low As Reasonably Practicable (ALARP). Standard IEC 60601-2-65, requires specific collimation limits such that the majority of the radiation from the x-ray source should be directed and limited to the detector surface, thus reducing the radiation burden to the patient. This requires a collimator (also known as a beam limiting device) that precisely controls the radiation field, and alignment of the radiation field and the detector. An x-ray source array with a plurality of the spatially distributed focal spots is difficult to collimate without moving the collimation assembly because the x-ray radiation is emitted from different focal spots on the x-ray anode. Thus, a new design of a collimation system that can meet this requirement is needed.

For conventional 2D intraoral radiography, two types of collimation are commonly used. One is a circular collimator which defines a radiation field that is significantly larger than the size of the intraoral sensor used. The large radiation field makes it easier and faster for the operator in the clinic to position the intraoral sensor and to minimize the chances of image truncation (also known as "cone cut"). With the large circular collimator, it is possible for an operator to place and position the intraoral detector without the use of an alignment guide. This reduces the imaging time, which is desirable for a busy dental clinic. The use of an oversized radiation field, which exposes the patient to more radiation, is possible because most of the conventional intraoral radiography equipment and intraoral detectors are sold separately. As such, the IEC requirement, discussed hereinabove, does not apply.

The other common type of collimation for 2D intraoral radiography is a rectangular collimator which defines a small radiation field that closely matches the size of the detector. It reduces the radiation exposure to the patient. In this case an alignment guide is commonly used to ensure that the detector is precisely aligned with the radiation field, to minimize the chance of cone cuts.

For the dental clinics, it is desirable to have collimators with small and large radiation fields that are easily interchangeable at the clinics.

An intraoral tomosynthesis device requires a dynamic intraoral detector that can synchronize image capturing with x-ray exposure at a high speed. Such a detector is not commonly available in dental clinics and is supplied as an integral part of the intraoral tomosynthesis imaging system. To follow the ALARP principle and to satisfy the IEC requirement, it is necessary to invent a collimation system that can collimate the x-ray radiation from all x-ray focal spots to the detector area for tomosynthesis imaging. It is further desirable that the collimation unit for the tomosynthesis system is stationary which does not need to mechanically move as the x-ray exposure is moved from one focal spot to another.

Furthermore, it is desirable that the intraoral tomosynthesis can also be used for conventional 2D intraoral radiography. When used for 2D intraoral radiography, it is desirable that the device provides options for circular collimation with a radiation field substantially larger than the x-ray sensor for easy placement of the sensor, and/or a rectangular collimation with a radiation field that is comparable to the sensor area for reducing the radiation dose.

For an intraoral tomosynthesis device utilizing a distributed x-ray source array with one or more x-ray focal spots, it is necessary to have a control electronic unit that can regulate the x-ray tube current for each of the one or more focal spots such that x-ray radiation from each x-ray focal spot is regulated.

A goal of the present disclosure is to address these clinical needs for intraoral tomosynthesis imaging.

SUMMARY OF THE INVENTION

In accordance with the disclosure herein, stationary x-ray intraoral tomosynthesis devices, systems, and methods are provided. The present disclosure describes, in some embodiments, designs of a stationary x-ray intraoral tomosynthesis imaging device and system with a detachable collimation assembly providing a variety of radiation fields for both 3-dimensional (3D) tomosynthesis imaging and regular 2-dimensional (2D) radiography. In other embodiments, the present disclosure includes methods to control the radiation from the plurality of x-ray focal spots.

In one aspect, an x-ray intraoral tomosynthesis imaging system is provided, the system comprising: an x-ray source array comprising one or more spatially distributed x-ray focal spots; an electronic unit comprising a high voltage power supply and a current source; a switching circuit configured to connect the current source to various cathodes of the x-ray source array, one at a time, to produce a scanning x-ray beam; a collimation assembly configured to provide rectangular or circular radiation fields; a digital intraoral x-ray detector; an input panel configured to allow a user to select x-ray energy, tube current, exposure time, and imaging mode, including a two dimensional (2D) imaging mode, a three dimensional (3D) imaging mode, or a combination of the 2D imaging mode and the 3D imaging mode; and an image viewer configured to display a stack of reconstructed tomosynthesis slice images, wherein the x-ray source array is configured to produce either a scanning x-ray beam illuminating an object from different viewing angles without mechanically moving the x-ray source array for tomosynthesis, or a single 2D radiograph; and wherein the collimation assembly is further configured to substantially collimate x-ray radiation from all x-ray focal spots to the digital intraoral x-ray detector.

In another aspect, the collimation assembly comprises: a primary collimator positioned close to an exit window of the x-ray source array wherein the primary collimator comprises an array of one or more apertures, each of the one or more apertures being aligned with one corresponding x-ray focal spot of the x-ray source array, and configured to allow x-ray radiation from the one corresponding x-ray focal spot to pass through; a secondary collimator positioned in line with respect to the primary collimator, wherein the secondary collimator has one aperture configured to further confine x-ray radiation passing through the primary collimator; and a cone structure that encloses the primary collimator and the secondary collimator.

In yet another aspect of the subject matter of the present disclosure, a method for x-ray intraoral tomosynthesis imaging is provided, the method comprising: providing an x-ray source array comprising one or more spatially distributed focal spots; providing an electronic unit comprising a high voltage power supply and a current source; providing a switching circuit that is configured to connect the current source to various cathodes of the x-ray source array, one at a time, to produce a scanning x-ray beam; providing a collimation assembly configured to provide rectangular and circular radiation fields; providing a digital intraoral x-ray detector; providing an input panel that allows a user to select x-ray energy, tube current, exposure time, and imaging mode, including a 2D imaging mode, a 3D imaging mode, or a combination of the 2D imaging mode and the 3D imaging mode; illuminating an object from different viewing angles with a scanning x-ray beam generated by the x-ray source array, without mechanically moving the x-ray source array, for tomosynthesis or a single 2D radiograph; collimating x-ray radiation from all of the one or more spatially distributed focal spots to the digital intraoral x-ray detector using the collimation assembly; and providing an image viewer configured to display a stack of reconstructed tomosynthesis slice images.

Although some of the aspects of the subject matter disclosed herein have been stated hereinabove, and which are achieved in whole or in part by the presently disclosed subject matter, other aspects will become evident as the description proceeds when taken in connection with the accompanying drawings as best described hereinbelow.

BRIEF DESCRIPTION OF THE DRAWINGS

Features and advantages of the present subject matter will be more readily understood from the following detailed description which should be read in conjunction with the accompanying, example drawings that are given merely by way of explanatory and non-limiting example, and in which.

DETAILED DESCRIPTION OF THE INVENTION

The present disclosure describes a stationary x-ray intraoral tomosynthesis imaging device, and related systems and methods, with a collimation assembly that can provide a variety of radiation fields needed for different imaging modes, including, for non-limiting example, rectangular and circular fields for both 3-dimensional (3D) tomosynthesis imaging and regular 2-dimensional (2D) radiography.

Figure 1:
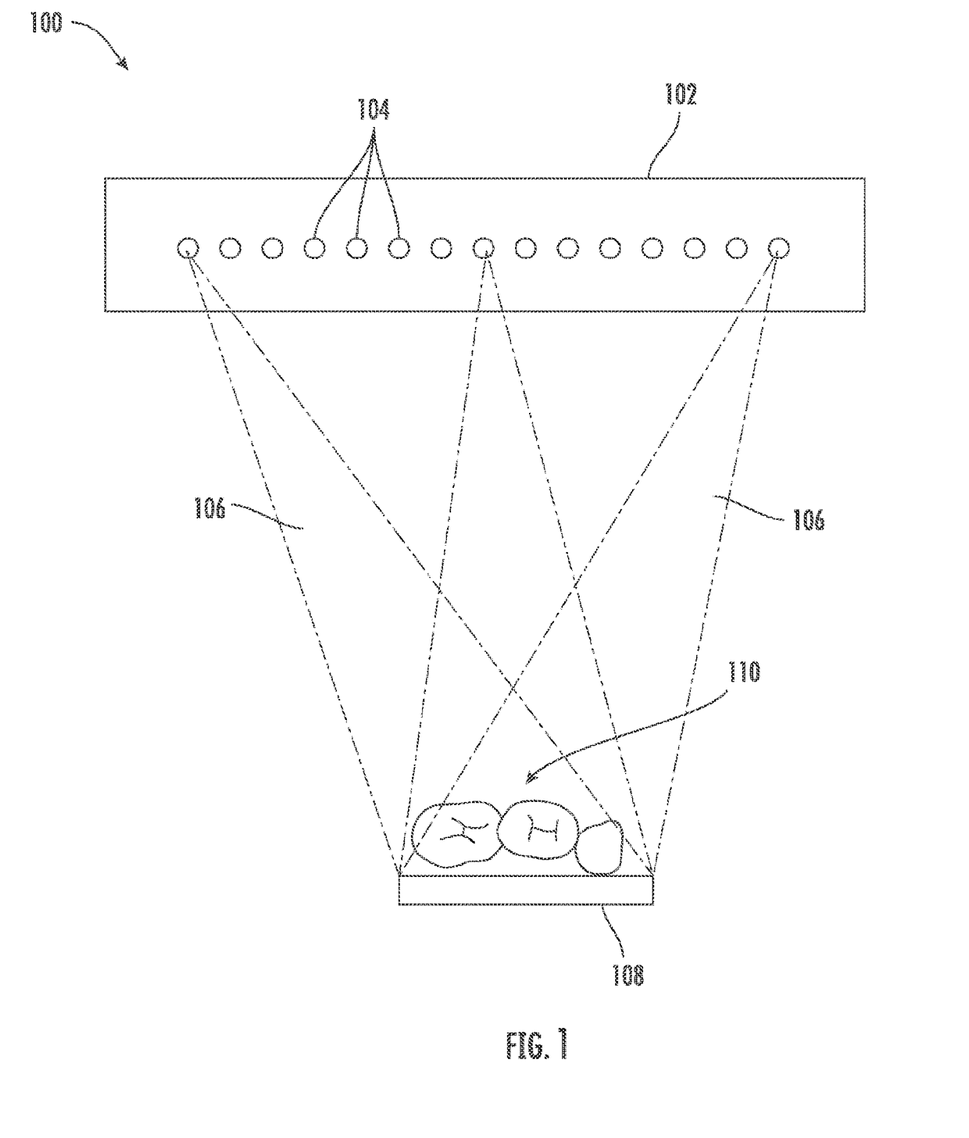
FIG. 1 is a schematic illustration of a test environment of the stationary intraoral tomosynthesis x-ray imaging device comprising a distributed x-ray source array and x-ray detector, according to an embodiment of the presently disclosed subject matter.

FIG. 1 of the drawings illustrates an example of a test environment generally designated 100 of the stationary intraoral tomosynthesis x-ray imaging device comprising an x-ray source array 102, one or more focal spots 104, exemplary x-ray beams 106, a digital intraoral x-ray detector 108, and a specimen 110, according to an embodiment of the presently disclosed subject matter. Those of ordinary skill in the art will appreciate that in order to generate an ideal x-ray image for diagnostic purposes, multiple projection images might be taken and then the final image is reconstructed and displayed. In some embodiments, the x-ray source array 102 generates all of the projection images needed for reconstruction without any mechanical movement of the x-ray source array 102 or the digital intraoral x-ray detector 108. In further embodiments of the present disclosure, the one or more focal spots 104 are spatially distributed about the x-ray source array 102.

In this embodiment, the x-ray source array 102 can be placed outside a patient's mouth and the intraoral x-ray detector 108 placed inside the patient's mouth wherein, the specimen 110 is positioned between the x-ray source array 102 and the intraoral x-ray detector 108. In this embodiment, the x-ray source array 102 emits x-ray beams 106 in the direction of the specimen 110 and the intraoral x-ray detector 108. The intraoral x-ray detector 108 detects the x-ray beams 106 and one or more images is/are generated based on those detections. In some embodiments, the x-ray source array 102 can be constructed using, for non-limiting example, carbon nanotube (CNT) field emission x-ray technology.

Figure 2A:
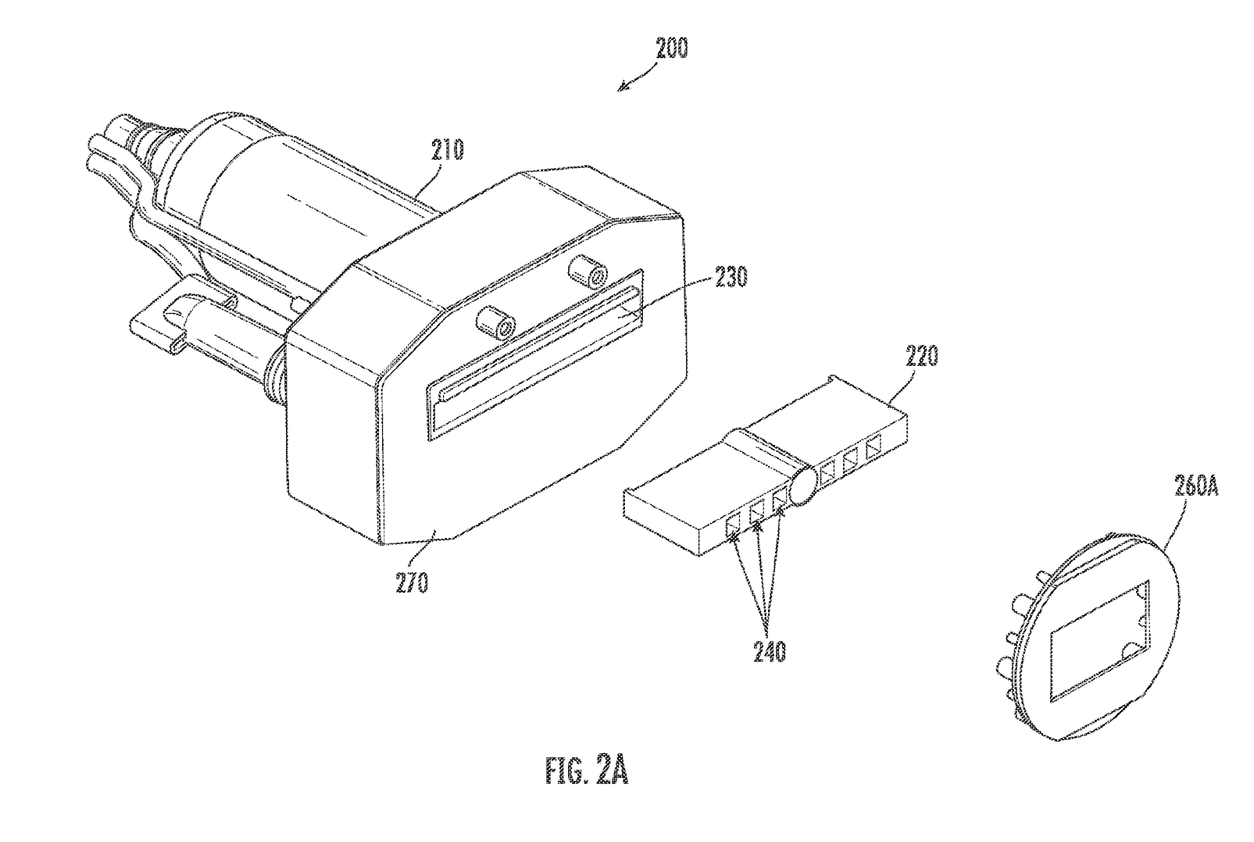
FIGS. 2A, 2B and 2C illustrate a perspective view of the stationary intraoral tomosynthesis x-ray imaging device with collimators assembled and the primary collimator attached on the device.
Figure 2B:
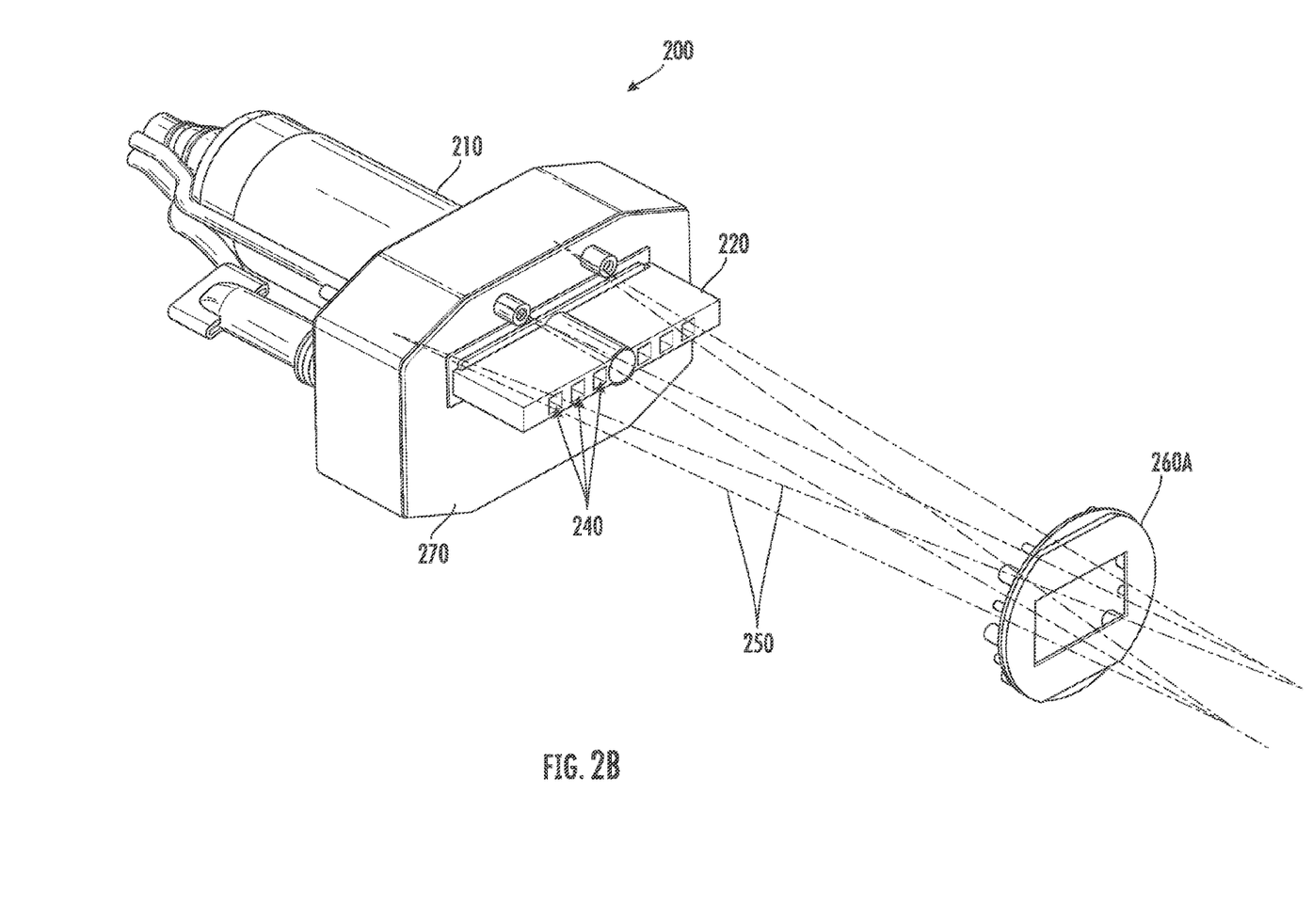

FIG. 2A of the drawings illustrates a partially exploded view of x-ray intraoral tomosynthesis imaging device generally designated 200 comprising a body 210, the x-ray source array 102 (inside the body 210 and not shown in this figure), a primary collimator 220 that fits into exit window 230, and a first secondary collimator 260A. In some embodiments, the primary collimator 220 is fixed to the front surface 270 inside the exit window 230, which can, for example and without limitation, mean the primary collimator 220 cannot be detached by an operator in the clinic. In some embodiments, the exit window 230 is positioned near the top of a front surface 270 of the body 210. In other embodiments of the present disclosure, the primary collimator 220, the first secondary collimator 260A, and/or a second secondary collimator 260B (as shown in FIG. 2B) are referred to together as a collimation assembly. Thus, when reference is made, hereinbelow, to a collimation assembly, it should be understood to those of ordinary skill in the art that, in some embodiments, the collimation assembly comprises the primary collimator 220, the first secondary collimator 260A, and/or the second secondary collimator 260B.

Figure 2C:
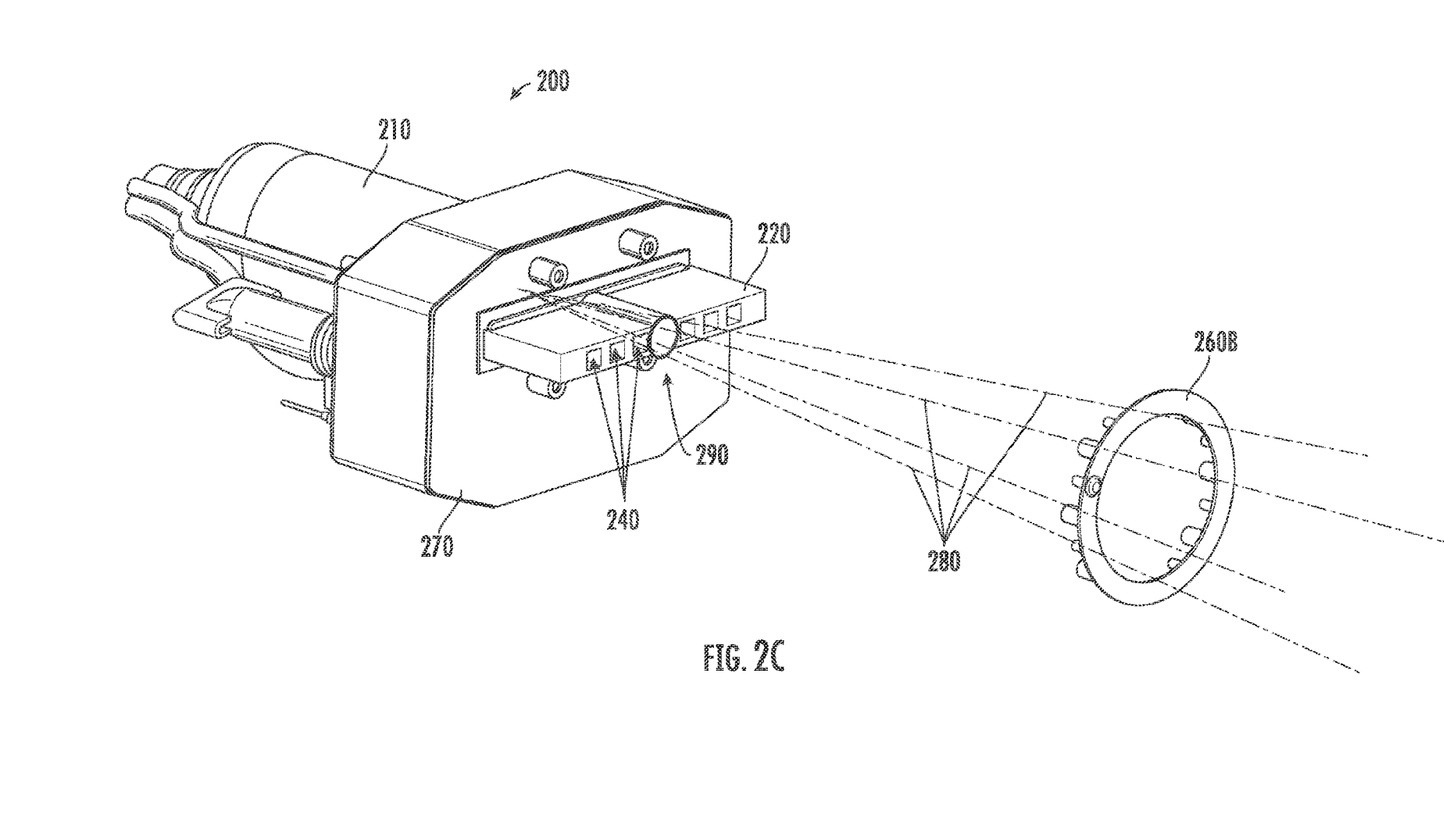

In other embodiments, the collimation assembly comprises the primary collimator 220 and the first secondary collimator 260A. In still other embodiments the collimation assembly comprises the primary collimator 220 and the second secondary collimator 260B. In some embodiments, the collimation assembly acts as a beam-limiting device for the x-ray beams emitted by the x-ray source array 102. In some embodiments, the x-ray intraoral tomosynthesis imaging device 200 is a stationary device. In other embodiments, the x-ray intraoral tomosynthesis imaging device 200 is non-stationary. In further embodiments of the present disclosure, the collimation assembly is further configured to substantially collimate x-ray radiation from all of the one or more x-ray focal spots 104 to the digital intraoral x-ray detector 108.

In some embodiments, and as briefly disclosed above, the primary collimator 220 is placed close to the exit window 230 of the x-ray source array 102. In some embodiments, the primary collimator 220 comprises one or more apertures such as apertures 240. Each of the one or more apertures 240 is aligned with a corresponding focal spot 104 of the x-ray source array 102, only allowing the x-ray radiation or x-ray beams from the corresponding focal spot 104 to pass through the corresponding aperture 240. In other words, each of the one or more apertures 240 of the primary collimator 220 is lined up with one focal spot 104 such that any x-ray radiation or x-ray beam emitted by a focal spot 104 is directed at or towards the aperture 240 that the focal spot 104 is lined up with. This is illustrated in FIG. 2B and FIG. 2C by lines 250. These lines 250 are illustrations of radiation or x-ray beams sent by the left most focal spot 104 of the x-ray source array 102 and exiting the left-most aperture 240.

FIG. 2B illustrates x-ray intraoral tomosynthesis imaging device 200 of FIG. 2A, but with the primary collimator 220 slid into the exit window 230. Additionally, FIG. 2B illustrates first secondary collimator 260A. In some embodiments, the first secondary collimator 260A is placed in line with the primary collimator 220. The first secondary collimator 260A has a single aperture (opening) that further limits the x-ray radiation or x-ray beams passing through the primary collimator 220. In some embodiments, the first secondary collimator 260A is rectangular in shape and/or is configured to provide rectangular radiation fields.

In some embodiments, the primary collimator 220 is mechanically fixed to the front surface 270 of the body 210 of the x-ray intraoral tomosynthesis imaging device 200 to ensure precise alignment of the one or more apertures 240 with the one or more focal spots 104. In further embodiments, the first secondary collimator 260A is configured such that it can be readily exchanged in a dental clinic, depending on the imaging needs of an operator of the x-ray intraoral tomosynthesis imaging device 200. In the embodiment shown in FIG. 2B, the first secondary collimator 260A is given a rectangular aperture for non-limiting, exemplary purposes only. In this exemplary embodiment, the rectangular aperture of the first secondary collimator 260A is used for tomosynthesis imaging.

FIG. 2C illustrates the x-ray intraoral tomosynthesis imaging device 200 of FIGS. 2A and 2B, however, this illustration comprises second secondary collimator 260B. In some embodiments, second secondary collimator 260B is circular in shape and/or is configured to provide a circular radiation field. In some embodiments, second secondary collimator 260B is used for 2D radiography. In particular, the circular aperture of second secondary collimator 260B is used for 2D radiography without having to use an x-ray detector holder (discussed hereinbelow) or other means of precise alignment of the x-ray detector (discussed hereinbelow) with the radiation field. In some embodiments, for 2D radiography, the radiation or x-ray beams are generated by one of the one or more x-ray focal spots 104. In one embodiment, a center focal spot 104 is used for 2D radiography. In some aspects, the central aperture 290 of the primary collimator 220 is larger than the rest of the apertures 240. In another embodiment, the center aperture 290 has a circular opening. This allows the radiation or x-ray beams from the central focal spot 104, as illustrated from the diverging lines 280, to cover the aperture of the enlarged circular second secondary collimator 260B.

In some embodiments, the primary collimator 220, the first secondary collimator 260A, and/or the second secondary collimator 260B are made of x-ray attenuating materials. In further embodiments, the primary collimator 220, the first secondary collimator 260A, and/or the second secondary collimator 260B are made of non-lead containing heavy metals. In another embodiment, the primary collimator 220, the first secondary collimator 260A, and/or the second secondary collimator 260B are made from, for non-limiting exemplary purposes, tungsten containing polymer that heavily attenuates x-ray beams or x-ray radiation, and can be made from one or more molding.

In some embodiments, the first secondary collimator 260A has a tight rectangular aperture and the second secondary collimator 260B has a large circular aperture. In further embodiments of the present disclosure, the first secondary collimator 260A has a tight rectangular aperture configured to collimate radiation generated from all of the one or more x-ray focal spots 104 to a surface of the intraoral x-ray detector 108 thereby reducing a patient's radiation dose. In some embodiments, the first secondary collimator 260A and the second secondary collimator 260B have different lengths and are configured to allow intraoral imaging at different source-to-detector distances. In some embodiments, the collimation assembly is configured to be easily detached and reattached to the x-ray intraoral tomosynthesis imaging device 200 thereby allowing imaging at different modes. In further embodiments, the collimation assembly comprises one or more attachments, including a tomosynthesis collimator configured for intraoral tomosynthesis imaging using all of the one or more x-ray focal spots 104, a radiograph collimator configured for 2D radiographic imaging using a pre-selected x-ray focal spot 104, or a combination collimation assembly configured for imaging in both 2D and tomosynthesis modes.

Figure 3A:
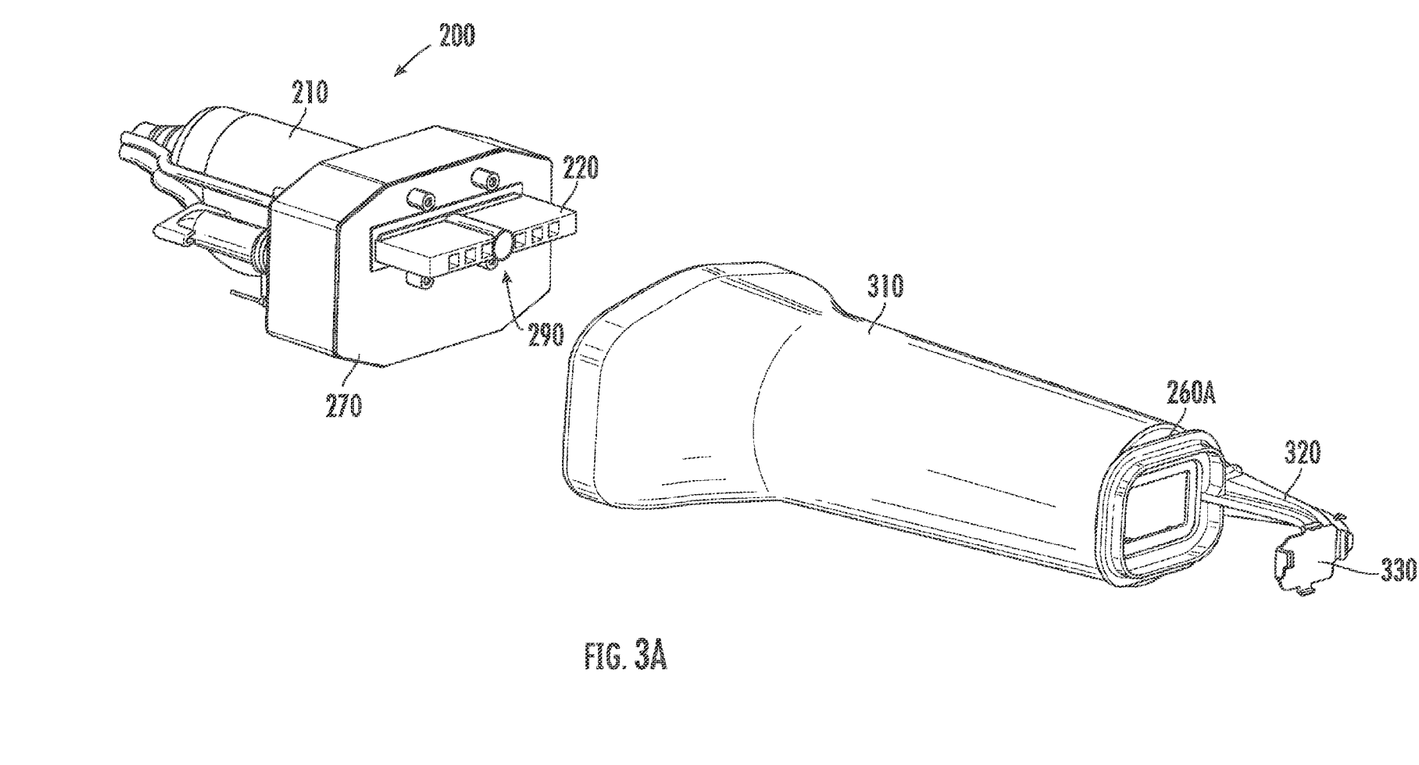
FIGS. 3A, 3B and 3C illustrate a perspective view of the stationary intraoral tomosynthesis x-ray imaging device with the primary and secondary collimators assembled and attached on the device as well as a housing.
Figure 3B:
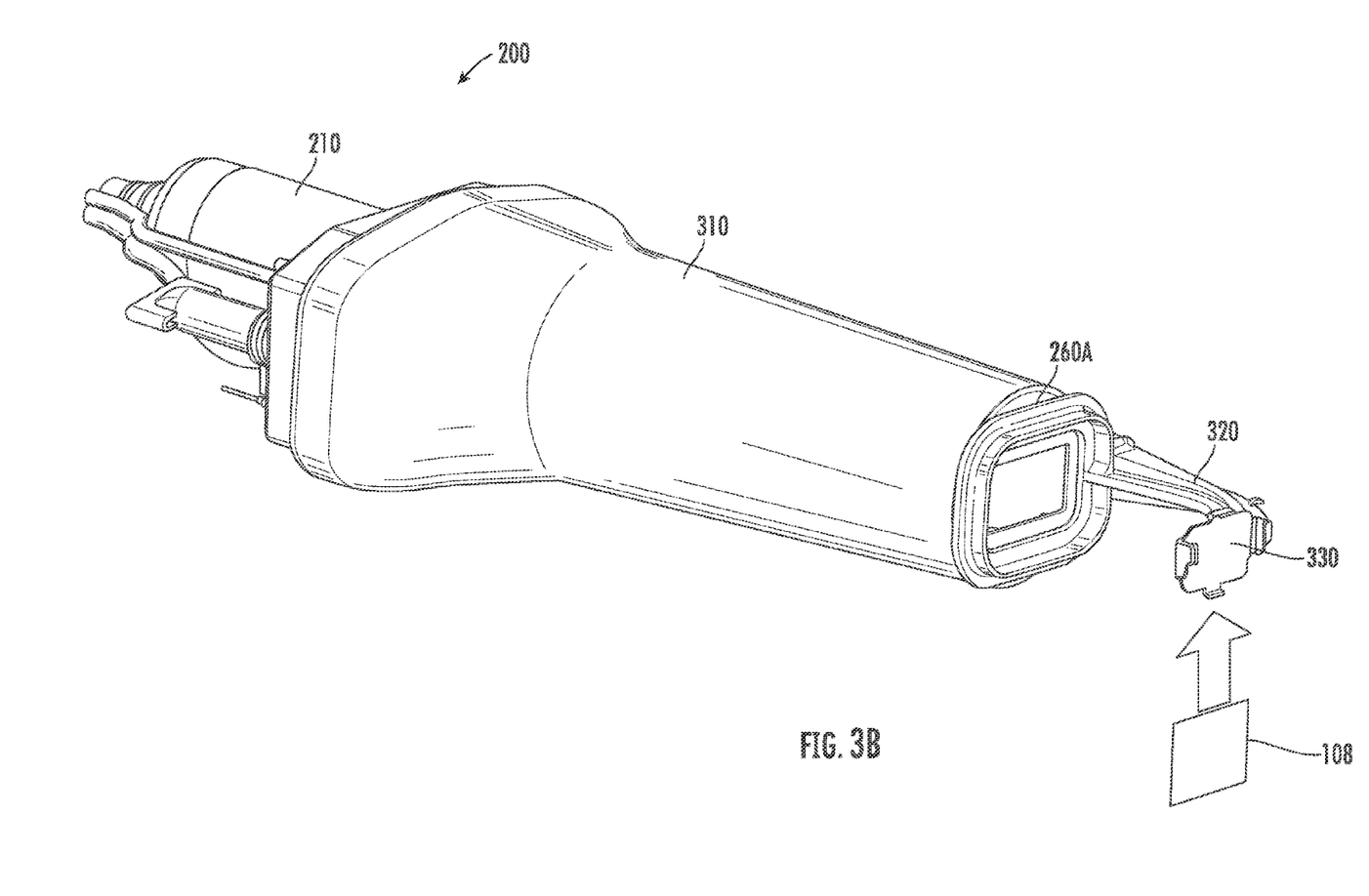

FIG. 3A illustrates the x-ray intraoral tomosynthesis imaging device 200 of FIGS. 2A through 2C. However, in some embodiments, as illustrated in FIG. 3A, the x-ray intraoral tomosynthesis imaging device 200 comprises an enclosure 310 that encloses the primary collimator 220, and, depending on which secondary collimator is being utilized, the first secondary collimator 260A or the second secondary collimator 260B. FIG. 3A illustrates the enclosure 310 detached from the body 210 of the x-ray intraoral tomosynthesis imaging device 200. However, FIG. 3B illustrates the housing 310 attached to the body 210. In one embodiment of the present disclosure, the first secondary collimator 260A is attached to a distal end of the enclosure 310. In another embodiment of the present disclosure, the second secondary collimator 260B is attached to a distal end of the enclosure 310 (not shown).

Figure 3C:
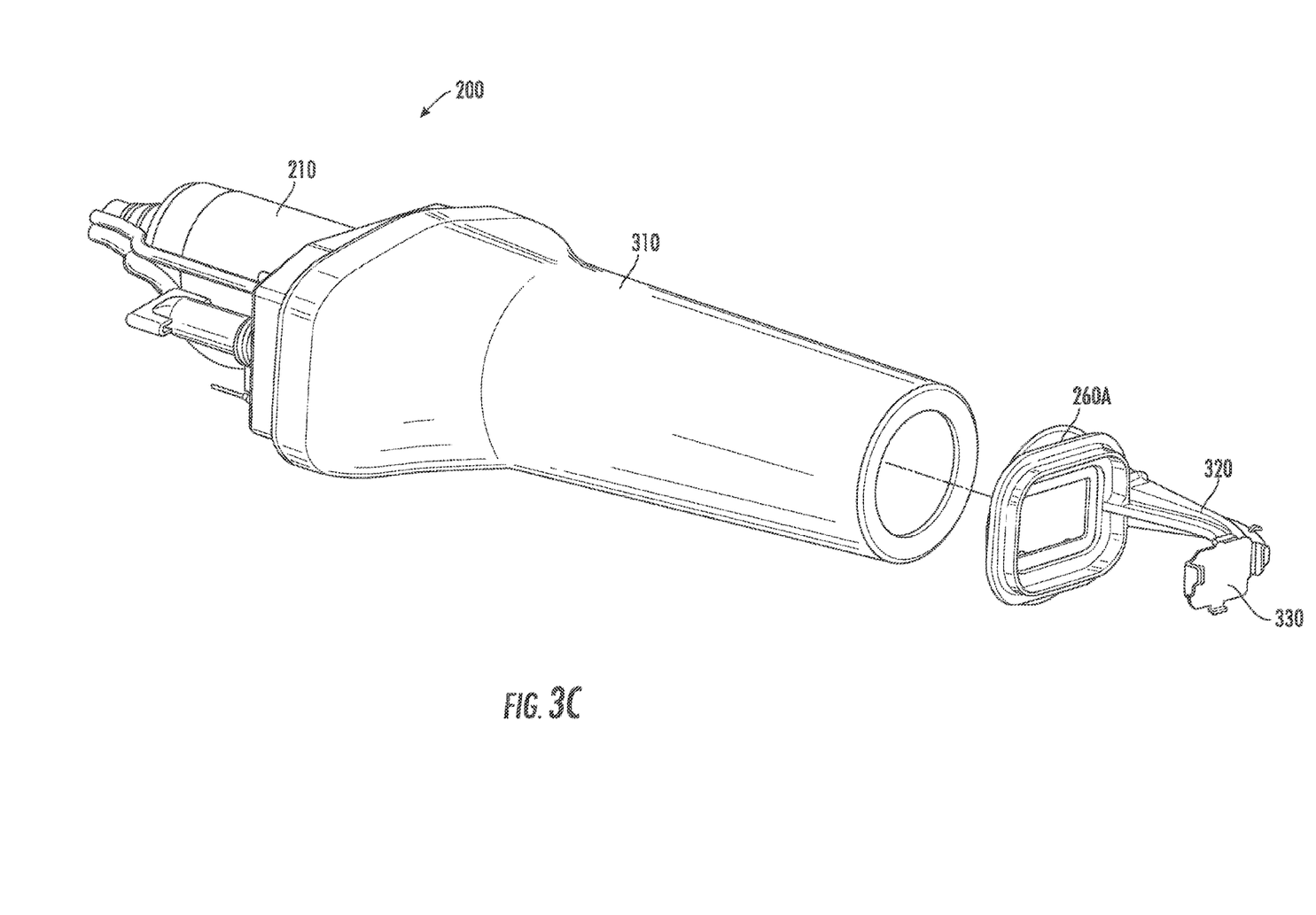

FIG. 3C illustrates that in some embodiments, the first secondary collimator 260A or the second secondary collimator 260B is connected to the enclosure 310 by a magnetic connection. Thus, in such an embodiment, the first secondary collimator 260A, the second secondary collimator 260B or any other secondary collimator can readily be detached or changed to another secondary collimator, without removing the enclosure 310 or the primary collimator 220.

FIG. 3B further illustrates that, in some embodiments, the x-ray intraoral tomosynthesis imaging device 200 comprises an x-ray detector holder 320 that is connected to the collimation assembly. In some aspects, the x-ray detector holder 320 is connected to the enclosure 310 by a magnetic connection. Thus, in such an embodiment, the x-ray detector holder 320 can be readily connected and disconnected from the enclosure 310. In some embodiments, the intraoral x-ray detector 108 can be attached to the x-ray detector holder 320 at the detector holder position 330. In some embodiments, when the intraoral x-ray detector 108 is inserted into the x-ray detector holder 320, and the x-ray detector holder 320 is property attached to the enclosure 310, the relative positions of the intraoral x-ray detector 108 with respect to the one or more x-ray focal spots 104 are fixed. In some embodiments, the x-ray detector holder 320 comprises biocompatible polymer. In further embodiments, the x-ray detector holder 320 is configured to be sanitized in an autoclave or by standard cleaning chemicals.

Figure 4:
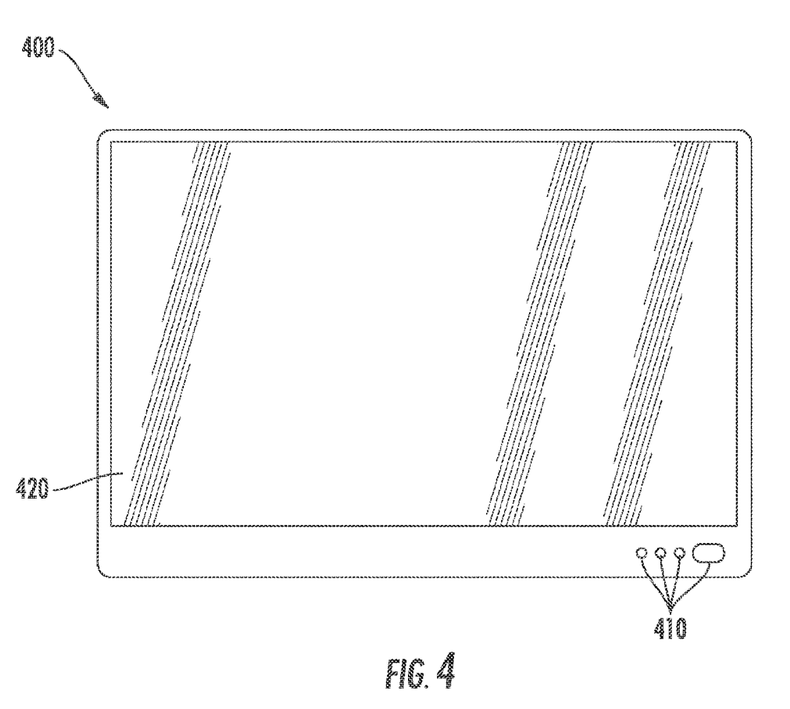
FIG. 4 illustrates an input panel and image viewer of the present disclosure.

FIG. 4 illustrates an input panel 400 that is configured to allow a user of the x-ray intraoral tomosynthesis imaging device 200 (not shown in this figure) to select the x-ray energy, tube current, exposure time, and/or the imaging mode of the x-ray intraoral tomosynthesis imaging device 200. In some embodiments, the input panel 400 comprises selection buttons 410 configured to allow a user to select the x-ray energy, tube current, exposure time, and/or the imaging mode of the x-ray intraoral tomosynthesis imaging device 200. In some embodiments, the user can select the imaging mode from a list comprising 2D imaging mode, 3D imaging mode, and/or a combination of 2D imaging mode and 3D imaging mode. In further embodiments, the input panel 400 comprises an image viewer 420 to display the stack of reconstructed tomosynthesis slice images.

In some embodiments, the image viewer 420 can, for example, be separate from the input panel 400. In some embodiments, the input panel 400 can, for non-limiting example, be affixed, or attached to a wall just outside the clinic room. In further embodiments, the input panel 400 can, for non-limiting example, be on a mobile station or mobile cart that can be taken from room to room. In some embodiments, the input panel 400 is connected to the x-ray intraoral tomosynthesis imaging device 200 by suitable cabling necessary to allow electronic communication between the input panel 400 and the x-ray intraoral tomosynthesis imaging device 200. In some embodiments, the input panel 400 comprises one or more processors and a non-transitory computer readable medium comprising tomosynthesis image reconstruction software used to reconstruct the tomosynthesis slice images.

Figure 5:
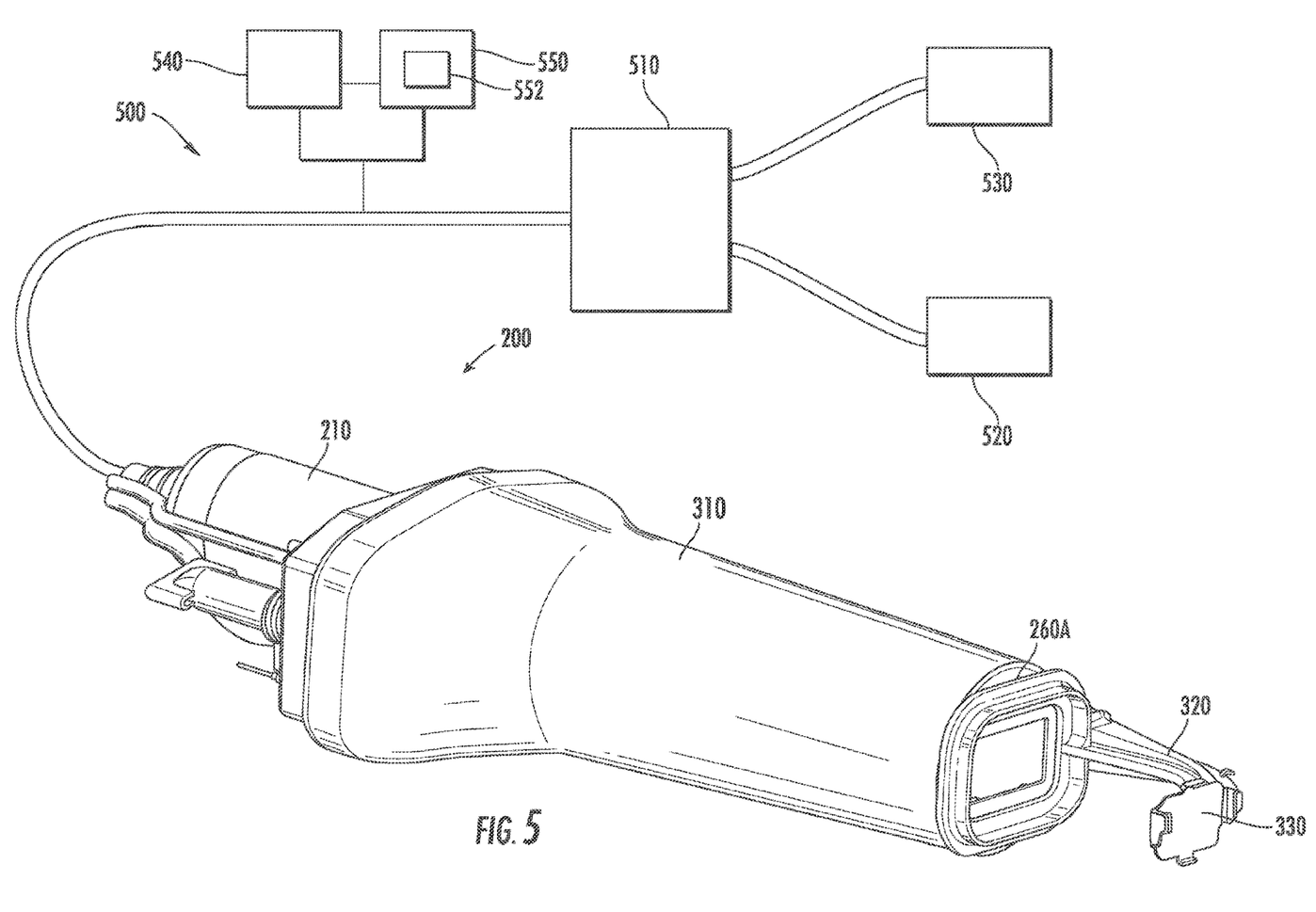
FIG. 5 illustrates the stationary intraoral tomosynthesis x-ray imaging device including a high voltage source and current source, as well as a switching circuit for the two sources.
Figure 6:
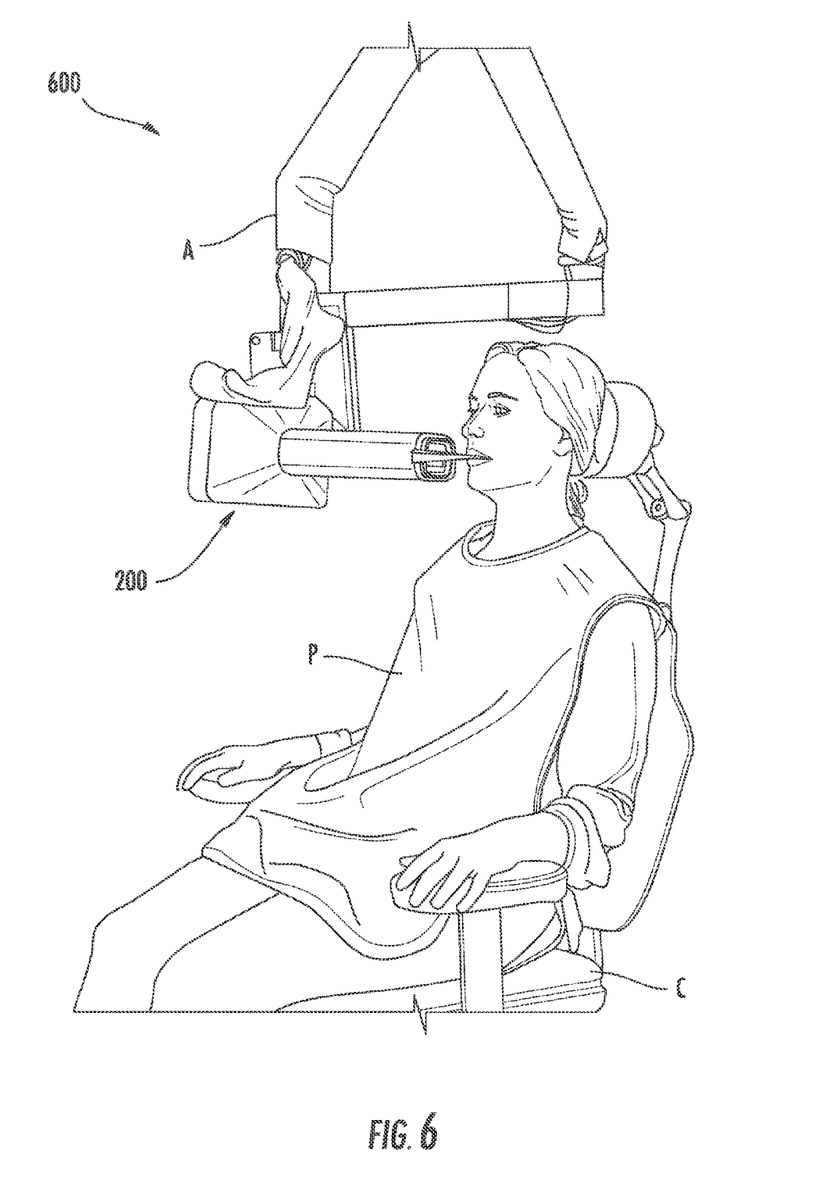
FIG. 6 illustrates the stationary intraoral tomosynthesis x-ray imaging device in a clinical setting with a patient in a dental chair.

FIG. 5 of the present disclosure illustrates an x-ray intraoral tomosynthesis imaging system 500 comprising the x-ray intraoral tomosynthesis imaging device 200 shown in FIG. 3B, a switching circuit 510, a current source 520, and a high voltage power supply 530. In some embodiments, the current source 520 and the high voltage power supply 530 are contained within an electronic unit (not shown). In some embodiments, the current source 520 and the high voltage power supply 530 are contained within a power supply (not shown). In some embodiments, the switching circuit 510 connects the current source 520 to various cathodes of the x-ray source array 102. In some embodiments, the switching circuit 510 can be configured to connect the current source 520 to the cathodes of the x-ray source array 102, for non-limiting example, one at a time, to produce a scanning x-ray beam. In some embodiments, the power supply is configured to provide the current source 520 to various cathodes of the x-ray source array 102, for non-limiting example, one at a time, as discussed above. The scanning x-ray beam, in some embodiments, illuminates an object from different viewing angles without mechanically moving the x-ray source array 102 for tomosynthesis, or a single 2D radiograph. In some embodiments, the high voltage power supply 530 is configured to power the entire x-ray intraoral tomosynthesis imaging system 500 and/or the input panel 400. In some embodiments, the x-ray intraoral tomosynthesis imaging system 500 comprises one or more processors 540 and a non-transitory computer readable medium 550 comprising tomosynthesis image reconstruction software 552 used to reconstruct the tomosynthesis slice images. FIG. 6 illustrates a test environment 600 comprising an x-ray intraoral tomosynthesis imaging device 200, and a patient P seated in a chair C at a dentist's office. The x-ray intraoral tomosynthesis imaging device 200 is suspended by arm A and positioned at the right cheek of the patient P. The x-ray detector holder 320 is placed inside the patient's P mouth such that intraoral x-ray detector 108 is positioned properly behind the patient's P specimen 110, for non-limiting example, a subset of the patient's teeth. In this position, the x-ray intraoral tomosynthesis imaging device 200 can be used on the patient P as disclosed hereinabove.

The present subject matter can be embodied in other forms without departure from the spirit and essential characteristics thereof. The embodiments described therefore are to be considered in all respects as illustrative and not restrictive. Although the present subject matter has been described in terms of certain preferred embodiments, other embodiments that are apparent to those of ordinary skill in the art are also within the scope of the present subject matter.

What is claimed is:

1. An x-ray intraoral tomosynthesis imaging system comprising:
    an x-ray source array comprising one or more spatially distributed x-ray focal spots configured to produce a scanning x-ray beam;
    a voltage power supply and a current source;
    a switching circuit configured to connect the current source to a plurality of cathodes of the x-ray source array, one at a time, to produce a scanning x-ray beam;
    a collimation assembly configured to provide rectangular or circular radiation fields;
    a digital intraoral x-ray detector;
    an input panel configured to allow a user to select one or more of x-ray energy, tube current, exposure time, and imaging mode; and an image viewer configured to display a stack of reconstructed tomosynthesis slice images, wherein the x-ray source array is configured to selectively produce either: (a) a scanning x-ray beam illuminating an object from different viewing angles without mechanically moving the x-ray source array for tomosynthesis; or (b) a single two dimensional (2D) radiograph; and wherein the collimation assembly is configured to substantially collimate x-ray radiation from all x-ray focal spots to the digital intraoral x-ray detector.

2. The system of claim 1, wherein the collimation assembly comprises:
a primary collimator positioned close to an exit window of the x-ray source array wherein the primary collimator comprises an array of one or more apertures, each of the one or more apertures being aligned with one corresponding x-ray focal spot of the x-ray source array, and configured to allow x-ray radiation from the one corresponding x-ray focal spot to pass through;
a secondary collimator positioned in line with respect to the primary collimator, wherein the secondary collimator has one aperture configured to further confine x-ray radiation passing through the primary collimator; and
a cone structure that encloses the primary collimator and the secondary collimator.

3. The system of claim 2, wherein the primary collimator is fixed to the x-ray source array; and wherein the secondary collimator is attached to a distal end of the cone structure and can be removed and exchanged by an operator of the device.

4. The system of claim 2, wherein at least one of the apertures of the array of one or more apertures of the primary collimator is larger than a remainder of the array of one or more apertures; wherein x-ray radiation generated from the one corresponding x-ray focal spot is used for a 2D radiograph; and wherein the secondary collimator is large and circular.

5. The system of claim 1, wherein the collimation assembly comprises one or more detachable or interchangeable collimators.

6. The system of claim 5, wherein the one or more detachable or interchangeable collimators comprises a first detachable or interchangeable collimator with a tight rectangular aperture or a second detachable or interchangeable collimator with a large circular aperture.

7. The system of claim 5, wherein the one or more detachable or interchangeable collimators have different lengths and are configured to allow intraoral imaging at different source-to-detector distances.

8. The system of claim 1, wherein the collimation assembly comprises a tight rectangular aperture configured to collimate radiation generated from all of the one or more spatially distributed x-ray focal spots to a surface of the digital intraoral x-ray detector thereby reducing radiation dose.

9. The system of claim 1, wherein the collimation assembly comprises a circular aperture configured to collimate radiation generated from all of the one or more spatially distributed x-ray focal spots into a radiation field that is substantially larger than a size of the digital intraoral x-ray detector such that the digital intraoral x-ray detector can be readily aligned within the radiation field without an alignment apparatus.

10. The system of claim 1, wherein radiation from any one of the one or more x-ray focal spots of the x-ray source array is sufficient for a 2D radiography.

11. The system of claim 1, wherein the collimation assembly comprises one or more collimators that are molded, extruded, or three dimensionally (3D) printed using materials that do not contain lead.

12. The system of claim 1, wherein the collimation assembly is detachable and reattachable to the device thereby allowing imaging at different modes; and wherein the collimation assembly comprises one or more attachments, including a tomosynthesis collimator configured for intraoral tomosynthesis imaging using all of the one or more x-ray focal spots, a radiograph collimator configured for 2D radiographic imaging using a pre-selected x-ray focal spot, or a combination collimation assembly configured for imaging in both 2D and tomosynthesis modes.

13. The system of claim 1, wherein the imaging mode includes a 2D imaging mode, three dimensional (3D) imaging mode, or a combination of the 2D imaging mode and the 3D imaging mode.

14. An x-ray intraoral tomosynthesis imaging device comprising:
an x-ray source array comprising one or more spatially distributed focal spots configured to produce a scanning x-ray beam;
a collimation assembly configured to provide rectangular or circular radiation fields; and
a digital intraoral x-ray detector;
wherein the x-ray source array is configured to produce either a scanning x-ray beam, illuminating an object from different viewing angles without mechanically moving the x-ray source array for tomosynthesis, or a single 2D radiograph;
wherein the collimation assembly is configured to substantially collimate x-ray radiation from all focal spots to the digital intraoral x-ray detector; and
wherein the collimation assembly comprises a circular aperture configured to collimate radiation generated from all of the one or more spatially distributed x-ray focal spots into a radiation field that is substantially larger than a size of the digital intraoral x-ray detector such that the digital intraoral x-ray detector can be readily aligned within the radiation field without an alignment apparatus.

15. The device of claim 14, wherein the collimation assembly comprises:
a primary collimator positioned close to an exit window of the x-ray source array wherein the primary collimator comprises an array of one or more apertures, each of the one or more apertures being aligned with one corresponding x-ray focal spot of the x-ray source array, and configured to allow x-ray radiation from the one corresponding x-ray focal spot to pass through;
a secondary collimator positioned in line with respect to the primary collimator, wherein the secondary collimator has one aperture configured to further confine x-ray radiation passing through the primary collimator; and
a cone structure that encloses the primary collimator and the secondary collimator.

16. The device of claim 15, wherein the primary collimator is fixed to the x-ray source array; and wherein the secondary collimator is attached to a distal end of the cone structure and can be removed and exchanged by an operator of the device.

17. The device of claim 15, wherein at least one of the apertures of the array of one or more apertures of the primary collimator is larger than a remainder of the array of one or more apertures; wherein x-ray radiation generated from the one corresponding x-ray focal spot is used for a 2D radiograph; and wherein the secondary collimator is large and circular.

18. The device of claim 14, wherein the collimation assembly comprises one or more detachable or interchangeable collimators.

19. The device of claim 18, wherein the one or more detachable or interchangeable collimators comprises a first detachable or interchangeable collimator with a tight rectangular aperture or a second detachable or interchangeable collimator with a large circular aperture.

20. The device of claim 18, wherein the one or more detachable or interchangeable collimators have different lengths and are configured to allow intraoral imaging at different source-to-detector distances.

21. The device of claim 14, wherein the collimation assembly comprises a tight rectangular aperture configured to collimate radiation generated from all of the one or more spatially distributed x-ray focal spots to a surface of the digital intraoral x-ray detector thereby reducing a patient's radiation dose.

22. The device of claim 14, wherein radiation from any one of the one or more x-ray focal spots of the x-ray source array is sufficient for a 2D radiography.

23. The device of claim 14, wherein the collimation assembly comprises one or more collimators that are molded, extruded, or 3-D printed using materials that do not contain lead.

24. The device of claim 14, wherein the collimation assembly is detachable and reattachable to the device thereby allowing imaging at different modes; and wherein the collimation assembly comprises one or more attachments, including a tomosynthesis collimator configured for intraoral tomosynthesis imaging using all of the one or more x-ray focal spots, a radiograph collimator configured for 2D radiographic imaging using a pre-selected x-ray focal spot, or a combination collimation assembly configured for imaging in both 2D and tomosynthesis modes.

* * * * *